US00PP34439P2

(12) United States Plant Patent
Karniel

(10) Patent No.: US PP34,439 P2
(45) Date of Patent: Jul. 26, 2022

(54) SEEDLESS TABLE GRAPE (GRAPEVINE) NAMED 'ARDTHIRTYEIGHT'

(50) Latin Name: *Vitis vinifera*
Varietal Denomination: 'ARDTHIRTYEIGHT'

(71) Applicant: AGRICULTURAL RESEARCH AND DEVELOPMENT LIMITED LIABILITY COMPANY, Bakersfield, CA (US)

(72) Inventor: Shachar Karniel, Bakersfield, CA (US)

(73) Assignee: Agricultural Research and Development Limited Liability Company, Bakersfield, CA (US)

( * ) Notice: Subject to any disclaimer, the term of this patent is extended or adjusted under 35 U.S.C. 154(b) by 0 days.

(21) Appl. No.: 17/803,068

(22) Filed: Jan. 31, 2022

(51) Int. Cl.
*A01H 6/88* (2018.01)
*A01H 5/08* (2018.01)

(52) U.S. Cl.
USPC ..... Plt./207

(58) Field of Classification Search
USPC ..... Plt./207
See application file for complete search history.

*Primary Examiner* — Annette H Para
(74) *Attorney, Agent, or Firm* — Lewis Roca Rothgerber Christie LLP

(57) ABSTRACT

A new distinct variety of grapevine named ARDTHIRTYEIGHT abundantly forms attractive crunchy seedless elongated berries with a yellow-green skin coloration, medium density and medium sized clusters which display a naturally sweet flavor which is ready for harvesting during August in San Joaquin Valley of Central California, U.S.A, and displays good eating qualities as a table grape, having a firmness amenable for handling, shipping, and storage.

1 Drawing Sheet

Classification: The present invention relates to a new *Vitis vinifera* Grapevine.

Variety denomination: The new Grapevine has a varietal denomination 'ARDTHIRTYEIGHT'.

BACKGROUND OF THE INVENTION

This invention relates to a new and distinct variety of *Vitis vinifera* and is a mutation of the ARRAFIFTEEN variety. A breeding program was initiated during the late 1990's near Bakersfield in the San Joaquin Valley of Central California. In 2010, during this breeding program, a spontaneous mutation of the ARRAFIFTEEN variety was discovered.

TABLE 1

ARDTHIRTYEIGHT compared with parent & closely related variety:

| Variety/ Characteristic | ARDTHIRTY-EIGHT | ARRA-FIFTEEN | AUTUMN KING |
|---|---|---|---|
| Skin | Medium | Thin | Medium |
| Berry shape | Crunchy | Crispy, Meaty and Juicy | Meaty & Soft |
| Berry size | 21 mm × 40 mm | 22 mm × 33 mm | 24 mm × 29 mm |

The parentage of the new variety can be summarized as follows:

ARRAFIFTEEN

The new variety of the present invention was found as a mutation during asexual propagation in 2010 near Bakersfield in the San Joaquin Valley of Central California, U.S.A. by bud grafting on mature Thompson rootstock (non-patented in the United States).

It was found that the new grapevine of the present invention possesses the following combination of characteristics:

(a) Forms attractive crunchy seedless elongated berries with a yellow-green skin coloration; in medium density and medium sized clusters which display a naturally sweet flavor, (b) Commonly bears fruit during the month of August in the San Joaquin Valley of Central California, U.S.A., and (c) Bears fruit that is firm and is well amenable for storage, handling, and shipping.

(d) Produces 40 bunches per vine, and an average of about 1-2 bunches per shoot, at a total of 48 lbs. fruit per vine.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2012 near Bakersfield in the San Joaquin Valley of Central California, U.S.A. by bud grafting on mature Thompson rootstock (non-patented in the United States). Such asexual propagation has been conducted thereafter in successive years to date and has shown that the characteristics of the new variety are strictly transmissible from one generation to another. Accordingly, the new variety undergoes asexual propagation in a true to type manner.

SUMMARY OF THE INVENTION

The new variety ARDTHIRTYEIGHT is a white seedless table grape with a high production, e.g., about 40 bunches per vine, and an average of about 1-2 bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWING

The accompanying photographic illustration shows typical six-year-old specimens of the new variety, vegetatively propagated, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of ARDTHIRTYEIGHT.

DETAILED BOTANICAL DESCRIPTION

The chart used in the identification of colors is The RHS Colour Chart of The ROYAL HORTICULTURAL SOCIETY (3$^{rd}$ Edition). The description is based on the observation of plants growing on 'Thompson Seedless' rootstock outdoors near San Joaquin Valley of Central California, U.S.A.

| VINE CHARACTERISTICS: | |
|---|---|
| vigor | Vigorous upright shoots |
| productive capacity | Bearing at a natural, average capacity. Spur pruning. |
| trunk | Strong and developed. Diameter is 2.3 inches, measured at 9 inches above ground. Rough with a fibrous, shaggy exterior. Light maple brown coloring (greyed orange 166D) |

*Date of bud burst in Bakersfield, Calif.*—February 26$^{th}$.

| YOUNG SHOOT CHARACTERISTICS: | |
|---|---|
| Openness of tip | fully open |
| Density of prostrate hairs on tip | absent or very sparse |
| Anthocyanin coloration of prostrate hairs on tip | None (yellow green 149C) |
| Density of erect hairs on tip | absent or very sparse |

| YOUNG LEAF CHARACTERISTICS: | |
|---|---|
| Color of upper side of blade | yellow green 144A |
| Color of lower side of blade | yellow green 145A |
| Density of erect hairs between main veins on upper side of blade | sparse |
| Density of erect hairs between main veins on lower side of blade | absent or very sparse |
| Density of prostrate hairs on main veins on upper side of blade | absent or very sparse |
| Density of prostrate hairs on main veins on lower side of blade | sparse |

| SHOOT CHARACTERISTICS: | |
|---|---|
| Attitude (before tying) | semi-erect |
| Color of dorsal side of internodes | yellow green 144B |
| Color of ventral side of internodes | yellow green 144C |
| Color of dorsal side of nodes | yellow green 145A |
| Color of ventral side of nodes | yellow green 145B |
| Density of graat hairs on internodes | absent or very sparse |
| Density of prostrate hairs on internodes | absent or very sparse |
| Length of tendrils | 7.5 inches |
| Diameter of tendrils | 0.09 inches |
| Color of tendrils | yellow green 145A |
| Number of tendrils at bloom | 4 |
| Positioning of first flowering and fruiting node | the first bunch is in the 3rd node |
| Inflorescence number per flowering shoot | 1-2 |

| FLOWER CHARACTERISTICS: | |
|---|---|
| Reproductive organs | fully developed stamens and fully developed gynoecium |
| Flower length | 0.2 inches |
| Flower diameter | 0.1 inches |
| Pistil length | 0.08 inches |
| Pistil color | yellow green 144A |
| Pollen Amount | rich |
| Pollen color | yellow 11C |
| Stamen color | yellow green 144A |
| Stamen length | 0.17 inches |
| Number of stamen | 6 |

*First bloom in Bakersfield, Calif.*—April 27th.

*Date of full bloom in Bakersfield, Calif.*—May 5th.

| MATURE LEAF CHARACTERISTICS: | |
|---|---|
| Size of blade | 7.5 × 6 inches |
| Shape of blade | wedge-shaped |
| Base descriptors | wedge-shaped |
| Leaf margin | doubly serrate |
| Leaf apex | acute |
| Blistering of upper side of blade | absent or very sparse |
| Depth of upper lateral sinuses | shallow |
| Number of lobes (Only varieties with lobed leaves) | five |
| Arrangement of lobes of upper lateral sinuses | slightly overlapped |
| Arrangement of lobes of petiole sinus | half open |
| Length of teeth | 0.6 inches |
| Ratio length/width of teeth | medium |
| Shape of teeth | both sides straight |
| Density of prostrate hairs between main veins on lower side of blade | absent or very sparse |
| Density of erect hairs on main veins on lower side of blade | medium |
| Density of erect hairs between the main veins on upper side of blade | medium |
| Density of prostrate hairs on main veins on upper side of blade | absent or very sparse |
| Length of petiole compared to length of middle vein | moderately shorter |
| Top side color | yellow green 147A |
| Bottom side color | yellow green 147B |
| Texture of upper side of blade | little rough |
| Texture of lower side of blade | rough |
| Vein color on upper blade | yellow green 145B |
| Vein color on lower blade | yellow green 145D |
| Venation pattern for upper blade | netlike venation |
| Venation patten for lower blade | netlike venation |
| Petiole length | 3.9 inches |

-continued

| MATURE LEAF CHARACTERISTICS: | |
|---|---|
| Petiole diameter | 0.14 inches |
| Petiole color | yellow green 145A |
| Petiole texture | smooth |

*Date of beginning of berry ripening in Bakersfield Calif.*—July 16th.

| BUNCH CHARACTERISTICS: | |
|---|---|
| Size (peduncle excluded) | medium |
| Density of berries on bunch | medium |
| Bunch length | 5.8 inches |
| Bunch diameter | 4.5 inches |
| Length of peduncle of primary bunch | 1.5 inches |
| Diameter of peduncle of primary bunch | 0.11 inches |
| Peduncle of primary bunch color | yellow green 145B |
| Peduncle texture | smooth |
| Bunches per vine | 40 |
| Average bunch weight | 1.2 lbs |

| BERRY CHARACTERISTICS: | |
|---|---|
| Size | large |
| Length | 1.5 inches |
| Weight | 0.3 oz |
| Diameter | 0.7 inches |
| Shape | cylindrical |
| Color of skin (without bloom) | yellow green 150A |
| Flesh color | yellow green 145C |
| Brix | 21 |
| Titrabable acidity percentage | 0.7% |
| Juice | 3.4 pH |
| Ease of detachment from pedicel | moderately easy |
| Thickness of skin | medium |
| Anthocyanin coloration of flesh | none |
| Firmness of flesh | moderately firm |
| Particular flavor | natural sweet |
| Formation of seeds | none |
| Berries per bunch | 95 |

| PEDICEL CHARACTERISTICS: | |
|---|---|
| Length | 0.6 inches |
| Diameter | 0.1 inches |
| Color | yellow green 1440 |
| Pedicel texture | rough |

| WOODY SHOOT CHARACTERISTICS: | |
|---|---|
| Woody shoot texture | rough |
| Woody shoot color | greyed orange 165B |
| Woody shoot length | 72 inches |
| Diameter | 0.4 inches |
| Internode length | 4.2 inches |

*Market use of observed plants.*—Fresh market.

Age and growing conditions: Six years growing under Y system in South Joaquin Valley (hot, dry summers).

Shipping characteristics: Number of days fruit has been stored under specific conditions: Fruit was in cold storage. Stored in poly bags inside Styrofoam boxes with sulfur pads. After 30 Days: rachises were 60% green; 3% berry shattering; no berry wrinkling or cracks were apparent.

DNA profile: To further the characterize the new variety DNA was extracted from plant samples and a DNA profile was obtained at California Seed & Plant Lab, California USA using base pairs for 10 standard microsatellite DNA markers. The data is presented hereafter.

TABLE 2

DNA profile for ARDTHIRTYEIGHT

| Microsatellite DNA Marker | Allele Sizes in Base Pairs | |
|---|---|---|
| M1 | 228 | 238 |
| M2 | 249 | 249 |
| M3 | 179 | 194 |
| M4 | 216 | 220 |
| M5 | 273 | 273 |
| M6 | 145 | 151 |
| M7 | 187 | 205 |
| M8 | 247 | 255 |
| M9 | 214 | 214 |
| M10 | 237 | 247 |

The ARDTHIRTYEIGHT variety has not been observed under all possible environmental conditions to date. Accordingly, it is possible that the phenotypic expression may vary somewhat with changes in light intensity and duration, cultural practices, and other environmental conditions.

Additional information relating to plant and fruit disease and pest resistance or susceptibility has not been observed to date. Specification of the plant hardiness zone and the heat/cold resistance has not been observed to date.

What is claimed is:

1. A new and distinct grapevine, botanically known as *Vitis vinifera*, identified as ARDTHIRTYEIGHT, substantially as shown and described herein.

* * * * *

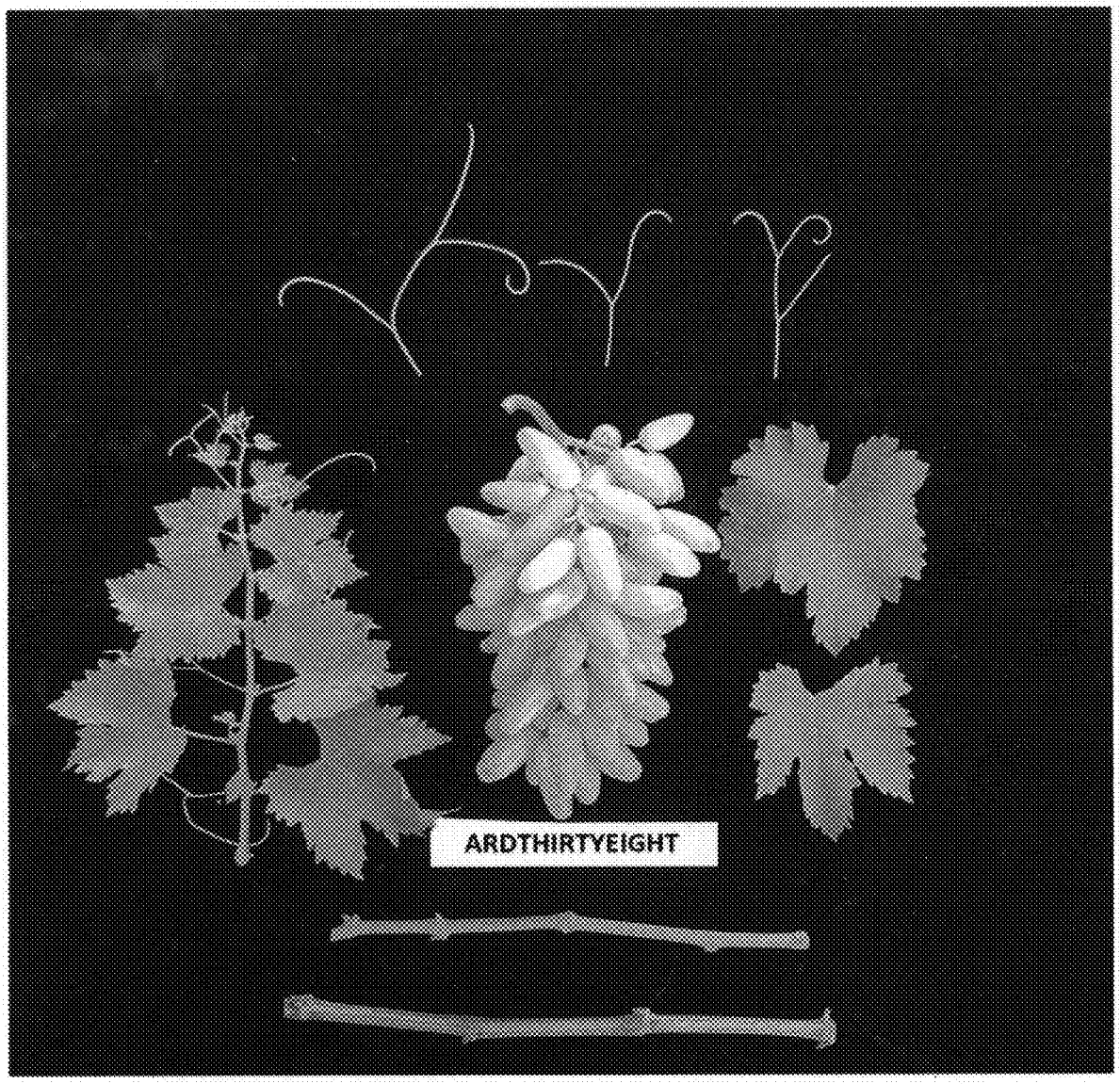
ARDTHIRTYEIGHT